US010575722B2

(12) United States Patent
Fiset

(10) Patent No.: US 10,575,722 B2
(45) Date of Patent: *Mar. 3, 2020

(54) CLEANING DEVICE FOR CLEANING A SCOPE, LAPAROSCOPE OR MICROSCOPE USED IN SURGERY OR OTHER MEDICAL PROCEDURES AND A METHOD OF USING THE DEVICE DURING SURGICAL OR OTHER MEDICAL PROCEDURES

(71) Applicant: Medix3d LLC, Santa Monica, CA (US)

(72) Inventor: Claude Fiset, Ojai, CA (US)

(73) Assignee: Medix3d LLC, Corona del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/110,035

(22) Filed: Aug. 23, 2018

(65) Prior Publication Data

US 2018/0360300 A1    Dec. 20, 2018

Related U.S. Application Data

(63) Continuation of application No. 14/966,622, filed on Dec. 11, 2015, now Pat. No. 10,080,488.

(60) Provisional application No. 62/091,466, filed on Dec. 12, 2014.

(51) Int. Cl.
*A61B 1/04* (2006.01)
*A61B 1/12* (2006.01)
*A61B 17/34* (2006.01)

(52) U.S. Cl.
CPC .............. *A61B 1/126* (2013.01); *A61B 1/127* (2013.01); *A61B 17/3417* (2013.01)

(58) Field of Classification Search
CPC ................................ A61B 1/126; A61B 1/127
USPC ................................ 600/104, 133, 157, 169
See application file for complete search history.

(56) References Cited

U.S. PATENT DOCUMENTS

| | | | |
|---|---|---|---|
| 4,392,485 A | 7/1983 | Hiltebrandt |
| 5,382,297 A | 1/1995 | Valentine et al. |
| 5,910,106 A | 6/1999 | Morgan et al. |
| 5,993,379 A | 11/1999 | Ouchi et al. |
| 6,503,192 B1 | 1/2003 | Ouchi |
| 7,080,641 B2 | 7/2006 | Gomez |
| 7,179,223 B2 | 2/2007 | Motoki et al. |
| 7,198,599 B2 | 4/2007 | Goto et al. |
| 7,311,660 B2 | 12/2007 | Gomez |
| 7,803,109 B2 | 9/2010 | Gomez |
| 7,922,650 B2 | 4/2011 | McWeeney et al. |
| 7,927,330 B2 | 4/2011 | Platt |
| 7,955,330 B2 | 6/2011 | Platt |
| 8,148,667 B2 | 4/2012 | Faries, Jr. et al. |
| 8,152,717 B2 | 4/2012 | Gomez |
| 8,185,997 B2 | 5/2012 | Heck |
| 8,353,815 B2 | 1/2013 | Okada |
| 8,452,068 B2 | 5/2013 | Averbuch et al. |
| 8,454,645 B2 | 6/2013 | Criscuolo et al. |
| 8,467,589 B2 | 6/2013 | Averbuch et al. |
| 8,517,918 B2 | 8/2013 | Smith |
| 8,535,220 B2 | 9/2013 | Mondschein |
| 8,540,745 B2 | 9/2013 | Criscuolo et al. |

(Continued)

*Primary Examiner* — Matthew J Kasztejna
(74) *Attorney, Agent, or Firm* — The Webb Law Firm

(57) ABSTRACT

A device and method for cleaning or defogging a surgical scope during minimally-invasive surgery, including a casing which houses a sponge and a heating element configured to be accessible to the surgical scope and the casing is configured to removably attach to a trocar during a surgical procedure.

18 Claims, 12 Drawing Sheets

(56) References Cited

U.S. PATENT DOCUMENTS

| | | |
|---|---|---|
| 8,696,552 B2 | 4/2014 | Whitman |
| 8,721,529 B2 | 5/2014 | Hess et al. |
| 8,727,969 B2 | 5/2014 | Leiner |
| 8,870,752 B2 | 10/2014 | Avitsian et al. |
| 9,060,676 B2 | 6/2015 | Blackhurst et al. |
| 9,078,694 B2 | 7/2015 | Hartoumbekis et al. |
| 2002/0022762 A1 | 2/2002 | Beane et al. |
| 2010/0168520 A1 | 7/2010 | Poll et al. |
| 2012/0184897 A1 | 7/2012 | Poll |
| 2012/0197084 A1 | 8/2012 | Drach et al. |
| 2013/0060086 A1 | 3/2013 | Talbert et al. |
| 2016/0135673 A1 | 5/2016 | Miller et al. |

… # CLEANING DEVICE FOR CLEANING A SCOPE, LAPAROSCOPE OR MICROSCOPE USED IN SURGERY OR OTHER MEDICAL PROCEDURES AND A METHOD OF USING THE DEVICE DURING SURGICAL OR OTHER MEDICAL PROCEDURES

CROSS REFERENCE TO RELATED APPLICATIONS

The present application is a continuation of U.S. patent application Ser. No. 14/966,622, filed on Dec. 11, 2015, entitled "CLEANING DEVICE FOR CLEANING A SCOPE, LAPAROSCOPE OR MICROSCOPE USED IN SURGERY OR OTHER MEDICAL PROCEDURES AND A METHOD OF USING THE DEVICE DURING SURGICAL OR OTHER MEDICAL PROCEDURES", which claims priority to U.S. Provisional Patent Application No. 62/091,466, filed on Dec. 12, 2014, entitled "CLEANING DEVICE FOR CLEANING A SCOPE, LAPAROSCOPE OR MICROSCOPE USED IN SURGERY OR OTHER MEDICAL PROCEDURES AND A METHOD OF USING THE DEVICE DURING SURGICAL OR OTHER MEDICAL PROCEDURES", each of which is hereby incorporated by reference in their entirety.

BACKGROUND OF THE INVENTION

Field of the Invention

The present application relates to a cleaning device for cleaning a scope, laparoscope, or microscope used in surgery or other medical procedures and a method of using the device during surgical or other medical procedures. The present application further relates to a cleaning kit for cleaning a trocar and a scope, laparoscope, or microscope, used in surgery or other medical procedures, and a method of using the kit during surgical or other medical procedures.

The following patents and patent publications are hereby incorporated by reference: U.S. Patent Application Publication No. 2012/0184897, having the title "INTEGRATED SYSTEMS AND METHODS FOR MAINTENANCE AND MANAGEMENT OF AN INTRA-ABDOMINAL GAS ENVIRONMENT DURING LAPAROSCOPIC SURGERY," published Jul. 19, 2012; U.S. Patent Application Publication No. 2012/0197084, having the title "SYSTEMS AND METHODS FOR OPTIMIZING AND MAINTAINING VISUALIZATION OF A SURGICAL FIELD DURING THE USE OF SURGICAL SCOPES," published Aug. 2, 2012; U.S. Patent Application Publication No. 2013/0060086, having the title "IMAGING SENSOR PROVIDING IMPROVED VISUALIZATION FOR SURGICAL SCOPES," published on Mar. 7, 2013; U.S. Patent Application Publication No. 2010/0168520, having the title "VIEW OPTIMIZER AND STABILIZER FOR USE WITH SURGICAL SCOPES," published Jul. 1, 2010; U.S. Pat. No. 8,535,220, having the title "LAPAROSCOPE CLEANING SYSTEM," issued Sep. 17, 2013; U.S. Pat. No. 4,392,485, having the title "ENDOSCOPE," issued on Jul. 12, 1983; U.S. Pat. No. 8,152,717, entitled "DEVICE FOR WHITE BALANCING AND APPLYING AN ANTI-FOG AGENT TO MEDICAL VIDEOSCOPES PRIOR TO MEDICAL PROCEDURES," issued on Apr. 10, 2012; U.S. Pat. No. 7,803,109, entitled "METHOD AND APPARATUS FOR PROTECTING THE DISTAL LENS OF ENDOSCOPES," issued on Sep. 28, 2010; U.S. Pat. No. 7,311,660, entitled "METHOD AND APPARATUS FOR HEATING AND APPLYING WARM ANTIFOG SOLUTION TO ENDOSCOPES AS WELL AS A DISTAL LENS PROTECTOR," issued on Dec. 25, 2007; U.S. Pat. No. 7,080,641, entitled "METHOD AND APPARATUS FOR HEATING STERILE SOLUTIONS DURING MEDICAL PROCEDURES," issued on Jul. 25, 2006; U.S. Pat. No. 8,870,752, entitled "MEDICAL DEVICE SHEATH," issued on Oct. 28, 2014; U.S. Pat. No. 8,727,969, entitled "ENDOSCOPE," issued on May 20, 2014; U.S. Pat. No. 8,696,552, entitled "SELF-CONTAINED STERILIZABLE SURGICAL SYSTEM," issued on Apr. 15, 2014; U.S. Pat. No. 8,540,745, entitled "BALLOON DISSECTOR WITH CANNULA," issued on Sep. 24, 2013; U.S. Pat. No. 8,517,918, entitled "OPTICAL TROCAR WITH SCOPE HOLDING ASSEMBLY," issued on Aug. 27, 2013; U.S. Pat. No. 8,467,589, entitled "HYBRID REGISTRATION METHOD," issued on Jun. 18, 2013; U.S. Pat. No. 8,454,645, entitled "BALLOON DISSECTOR WITH CANNULA," issued on Jun. 4, 2013; U.S. Pat. No. 8,452,068, entitled "HYBRID REGISTRATION METHOD," issued on May 28, 2013; U.S. Pat. No. 7,955,330, entitled "MULTI-PORT SIDE-FIRE COAGULATOR," issued Jun. 7, 2011; and U.S. Pat. No. 7,927,330, entitled "MULTI-PORT SIDE-FIRE COAGULATOR," issued Apr. 19, 2011.

During minimally invasive surgeries, such as laparoscopic surgery, trocars are used to permit access into a patient's body. Trocars are medical devices or instruments that comprise hollow tubes or hollow portions. During surgery, such as laparoscopic surgery, a trocar may be inserted through an incision into a patient's body, such as into the abdominal or pelvic cavity of a patient. The trocar acts as a passageway for other surgical tools or devices, such as scopes, laparoscopes, microscopes, knives, graspers, scissors, staplers, and more, to enter the body for use during surgery.

During such surgical procedures, the lenses of viewing devices inserted into the body through the trocar, such as scopes, laparoscopes and/or microscopes, may become clouded, or the view therethrough may become partially or completely obscured. The view can be obscured, either partially or completely, if the lenses are smeared with bodily fluids or the like, or if the lenses become clouded or fogged over due to the humidity within the body of the patient. In addition, the interior of the trocars should also be kept clean.

An object of the present application may be to provide a cleaning device for a trocar and surgical scopes, which cleaning device may be utilized during surgery. The cleaning device also may be used to defog lenses or optics of a surgical scope.

SUMMARY OF THE INVENTION

When minimally invasive surgeries are performed using trocars, the scopes and/or microscopes used during surgery, which often are inserted into the body of the patient, may become smeared with bodily fluids or the like. This may cause the lens of the scope or microscope to become obscured or clouded because of smearing and/or the humidity or moisture within the body of the patient. Embodiments of the cleaning device and method described herein address these problems. There may be other applications for the scope or microscope which create the same problems as with minimally invasive surgery, and embodiments of the device and method described below may be appropriate to address those problems as well.

An embodiment of the cleaning device according to the present application may be configured for cleaning a surgical scope during minimally invasive surgery. The cleaning device may comprise a casing which houses a sponge and a heating element, and an attachment element connected to an outer surface of the casing and configured to removably attach the casing to the trocar, wherein the casing is configured to allow a lens of the surgical scope to access the sponge and the heating element. In an embodiment, the casing may comprise a first depression formed in an upper surface of the casing and configured to receive the sponge therein and a second depression formed in an upper surface of the casing and configured to receive the heating element therein. In an embodiment the sponge may be impregnated with a cleaning medium. In an embodiment, the cleaning device may include a snap member that is configured to removably attach the casing to the trocar.

In an embodiment, the heating element may be comprised of a heating coil and at least one battery operatively connected to the heating coil, wherein the heating coil is configured to warm the lens of the surgical scope when the surgical scope is positioned in proximity to the heating coil. In an embodiment, the cleaning device may further comprise at least one light operatively connected to the at least one battery.

In an embodiment, the heating element may be comprised of a chemical pack.

An embodiment of the cleaning device described herein may comprise a cover and a wiping element, wherein the cover is disposed over the second depression, wherein the cover comprises a first hole, wherein a wiping element comprises a second hole; and wherein the wiping element is disposed over the cover so that the first hole and the second hole are oriented to allow the surgical scope to access the heating element. In an embodiment, the wiping element may be comprised of a microfiber material.

Another embodiment disclosed herein is a cleaning kit for use during minimally invasive surgery, comprising a container housing a sponge and configured to removably attach to the trocar, a cover comprising a scope access hole configured to permit a surgical scope to access the sponge, the cover positioned on an upper surface of the container; and a cannula cleaner comprising an elongated body having a first end having a cleaning tip disposed thereon and a second end, the cannula cleaner configured to be removably supported by at least one of the container and cover when not in use, wherein the cannula cleaner is configured for insertion in a cannula of a trocar and the cleaning tip is configured to contact the cannula when the cannula cleaner is inserted into the cannula. An embodiment of the cleaning kit may include a cannula cleaner wherein the elongated body further comprises a solution container configured to receive a cleaning medium, and a valve disposed on the second end of the elongated body, wherein the valve is configured to dispense the cleaning medium during surgery. In an embodiment the cleaning kit may comprise at least one wiping member disposed on the cover, wherein the at least one wiping member is configured to allow the surgical scope to access the sponge through the scope access hole. In an embodiment, the cleaning kit may further comprise a snap member configured to attach the container to the trocar.

In an embodiment, the cleaning kit may further comprise a heater disposed in the container, wherein the heater is configured to warm the surgical scope inserted through the scope access hole. In an embodiment, the heater is configured to border a substantial portion of a perimeter of the sponge. In an embodiment, the heater comprises a heating coil and at least one battery operatively connected to the heating coil, and the heating coil is configured to warm the lens of the surgical scope during surgery. In an embodiment, the heater may comprise a chemical pack.

In an embodiment, the cleaning kit may further comprise one or more lights operatively connected to at least one battery.

Another embodiment is directed to a method of cleaning a surgical scope during minimally invasive surgery, comprising inserting a trocar into a patient, attaching a cleaning device according to claim 3 to the trocar, heating a heating element of the cleaning device to a desired temperature, inserting the surgical scope into the trocar, removing the surgical scope from the trocar, wiping the lens of the surgical scope on the wiping element, and heating the lens of the surgical scope with the heating element. In an embodiment, this method further may comprise wiping the lens on the sponge.

One feature or aspect of an embodiment is using a cleaning device for cleaning laparoscopes used in a medical procedure, the cleaning device comprising a body with a snap device attached to said body, which snap device is configured to attach to a trocar; said body comprising an isosceles triangular shape with a longer side connecting the equal sides of the isosceles triangle with the snap device being attached to the middle of said longer side of the isosceles triangle; and the body comprising two hollowed out portions, one of said hollowed out portions being disposed on each side of said snap arrangement. A first hollowed out portion being configured to house a sponge impregnated with a cleaning solution, which cleaning solution is configured to clean off the tip portion of a laparoscope, where a lens is disposed, which tip portion is configured to be inserted into the trocar and into the body of the patient. A second hollowed out portion being configured to house a heating arrangement, which heating arrangement comprises a chemical heat pack and/or a battery-operated electric heating arrangement and a cover for the heating arrangement being disposed to form a closing side of said second hollowed out portion and being configured to provide an enclosure for the heating arrangement disposed in said second hollowed out portion. The cover comprising at least one of: a heat chamber cover, a microfiber holder, and a microfiber covering layer. The cover further comprises a hole therein being configured to receive a tip of a laparoscope. The procedure comprising: wetting said sponge by impregnating said sponge with cleaning solution, and disposing said impregnated sponge in said first hollowed out portion of said cleaning device; inserting said heating arrangement in said second hollowed out portion of said cleaning device; snapping said cleaning device onto the trocar and orienting said cleaning device toward a surgeon such that the apex of said isosceles triangle is disposed towards the surgeon or in some other direction than the apex being disposed towards said surgeon; heating the heating arrangement to a predetermined temperature; initially inserting a laparoscope into the trocar and into the body of a patient; proceeding with surgery until the lens portion of the laparoscope at its tip becomes smeared with the patient's bodily components or until the lens of the laparoscope is unusable because of condensation on the lens; removing the laparoscope from the trocar and wiping the lens on said impregnated sponge until the bodily components or condensate has been removed; inserting the tip of the laparoscope with its lens through said hole in said heat chamber cover; raising the temperature of the laparoscope tip sufficiently to minimize condensation on the laparoscope lens during a next phase of the surgical procedure; removing the tip of the laparoscope from said heating chamber and inserting the tip of the laparoscope into the trocar; continuing the surgical procedure with a cleaned laparoscope; and repeating the above cleaning operation when required.

Another feature or aspect of an embodiment is a cleaning device for cleaning laparoscopes during a medical procedure for performing laparoscopic surgery, said cleaning device comprising: a body with a snap device attached to said body, which snap device is configured to attach to a trocar; said body comprising an isosceles triangular shape with a longer side connecting the equal sides of the isosceles triangle; said snap device being attached to the middle of said longer side of the isosceles triangle; said body comprising two hollowed out portions, one of said hollowed out portions being disposed on each side of said snap arrangement. A first hollowed out portion being configured to house a sponge impregnated with a cleaning solution, which cleaning solution is configured to clean off the tip portion of a laparoscope, where a lens is disposed, which tip portion is configured to be inserted into the trocar and into the body of the patient. A second hollowed out portion being configured to house a heating arrangement, which heating arrangement comprises: a chemical heat pack and/or a battery-operated electric heating arrangement and a cover for the heating arrangement being disposed to form a closing side of said second hollowed out portion and being configured to provide an enclosure for the heating arrangement disposed in said second hollowed out portion; said cover comprising at least one of: a heat chamber cover, a microfiber holder, and a microfiber covering layer. The cover further comprising a hole therein being configured to receive a tip of a laparoscope.

For purposes of the description hereinafter, the spatial orientation terms and derivatives thereof shall relate to the embodiment as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments. Hence, specific dimensions and other physical characteristics related to the embodiments disclosed herein are not to be considered as limiting.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. As used in the specification and the claims, the singular form of "a", "an" and "the" include plural referents unless the context clearly dictates otherwise.

The above-discussed embodiments of the present invention will be described further herein below.

BRIEF DESCRIPTION OF THE DRAWING(S)

DESCRIPTION OF THE INVENTION

Figure 1:
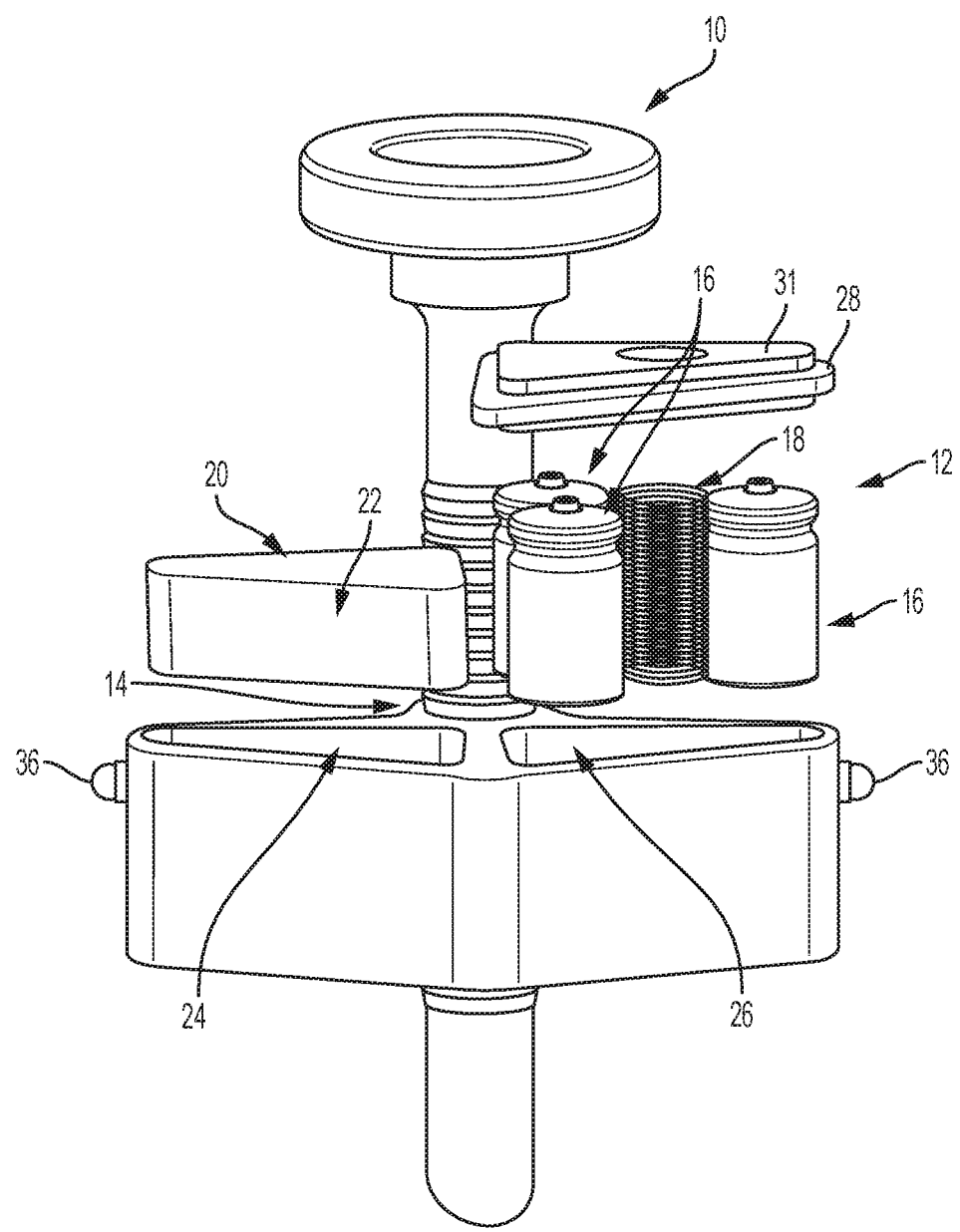
FIG. 1 shows an exploded front view of an embodiment of a cleaning device and a trocar used in at least minimally invasive surgery.

FIG. 1 shows a trocar 10 used in minimally invasive surgery. The trocar 10 has a cleaning device 12 removably connected thereto. The cleaning device 12 as shown is snapped onto to the trocar 10 using a snap member 14. However, this is not to be construed as limiting the present disclosure as any suitable attachment element, such as a hook-and-loop fabric, buckles, clips, tape, etc., configured to securely and removably attach the cleaning device 12 to the trocar 10 may be utilized.

An embodiment of cleaning device 12 is depicted in FIG. 1 in an exploded view. The cleaning device 12 comprises a casing 15 having the snap member 14 attached to an outside rear surface thereof. A first depression 24 may be formed in an upper surface of the casing 15 of cleaning device 12 to receive a sponge 20. In one example, the sponge 20 may be impregnated with a cleaning medium 22. The casing 15 may further include a second depression 26 formed in an upper surface thereof and disposed opposite the first depression 24. The second depression 26 may be configured to receive a heating element therein. In one example, the heating element can comprise batteries 16 and a heating coil 18 operatively connected to the batteries 16. The heating coil 18 may be configured to warm a microscope, laparoscope, or other surgical scope (not shown) so that the scope is ready for reinsertion in the trocar 10 and ready for reinsertion into the body of the patient being operated upon. Instead of batteries 16 and heating coil 18, a chemical pack housing chemicals that combine in an exothermic reaction, such as is used by skiers in their gloves to keep their hands warm while skiing, may be used as the heating element.

In one exemplary use of the cleaning device, the scope being utilized in a surgical procedure is removed from the trocar 10. It is first wiped off on the sponge 20, thereby to remove matter from the patient which has built up during the surgical procedure or which has condensed upon the scope during the surgical procedure. The heating element is then used to heat the front of the scope, thereby heating the front of the scope above the temperature of the patient to discourage the formation of condensate on the front of the scope when the scope is within the body of the patient. One or more lights 36, such as light emitting diode (LED), may be positioned on casing 15 and used to provide illumination for the trocar 10 and the site where the trocar 10 is inserted into a patient. The lights may be operatively connected to batteries 16.

Figure 2:
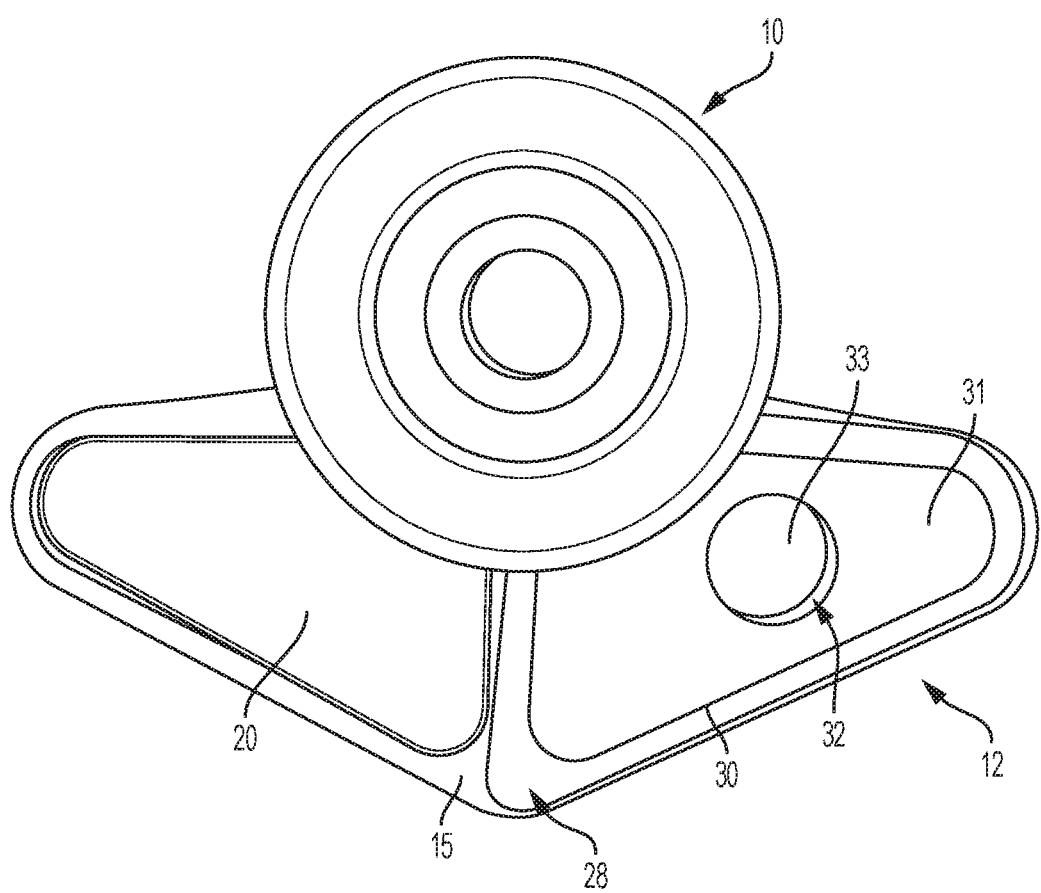
FIG. 2 is a top view of an embodiment of a cleaning device attached to a trocar.

FIG. 2 shows a top view of the cleaning device 12 attached to a trocar 10. The second depression 26 may further include a heating chamber cover 28 positioned over the top thereof to provide protection for the heating element. The heating chamber cover may further include a microfiber holder 30 formed therein configured to hold a microfiber cover 31. The heating chamber cover 28 and the microfiber cover 31 may be configured with at least one scope access hole 32 which permit the microscope or other scope to be inserted into heating chamber 33 to be warmed by heating coil 18, heating pack, or some other manner known in the art. Microfiber cover 31 may be used by surgical staff to wipe debris and/or fluids from a scope in order to clean the optics thereof prior to inserting the scope into the scope access hole 32 to be heated. In an embodiment, microfiber cover 31 may be disposed on heating chamber cover 28 within the holder 30 in order to provide easy access to surgical staff.

With further reference to FIG. 2, in one example, casing 15 may have a substantially isosceles triangular shape when viewed from above, with the two sides of the triangle that are not of equal length not adjacent to the trocar 10. Such a configuration may have the benefit of optimizing placement of the heating coil 18 and batteries 18 in casing 15 next to sponge 20. This configuration also may have the benefit of providing easy access to cleaning device 12 while minimizing interference of the device with access to the surgical site while the cleaning device 12 is attached to the trocar 10 during a surgical procedure.

Figure 3:
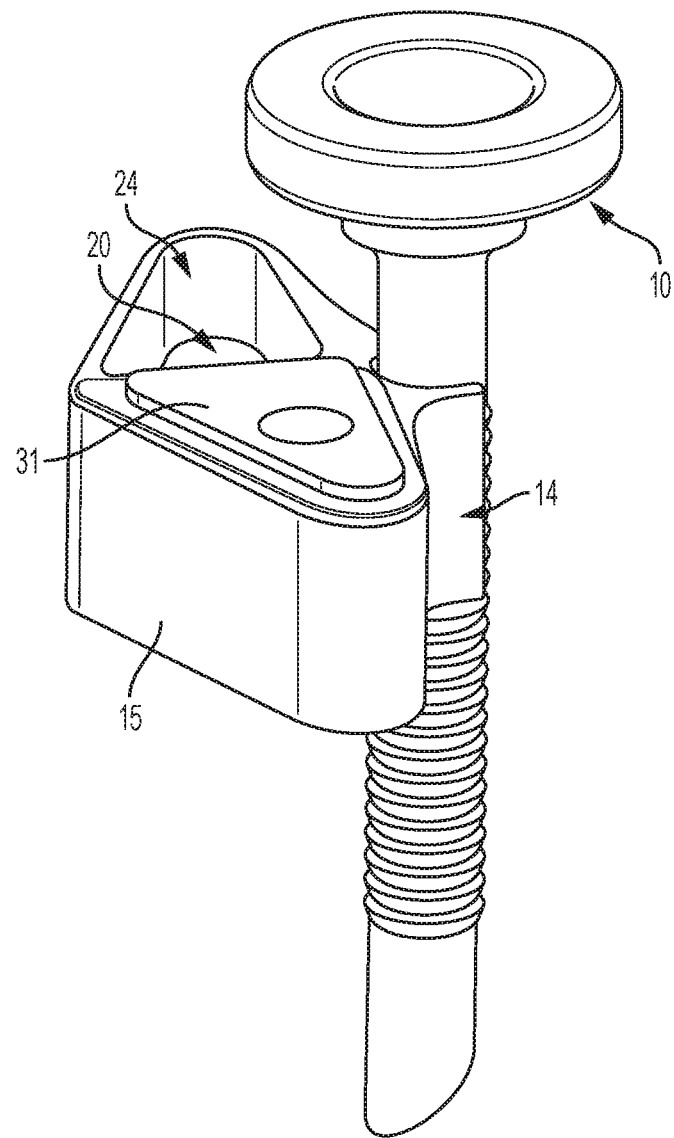
FIG. 3 shows a perspective view of an embodiment of a cleaning device attached to the trocar by the snap member.

In FIG. 3, the trocar 10 is shown again with the cleaning device 12 attached thereto by snap member 14. An advantage of such an embodiment is that it places cleaning device 12 in close proximity to trocar 10, and thereby provides easy access to surgical staff. Such an embodiment also has the advantage that cleaning device 12 does not need to be set on a separate tray.

Figure 4:
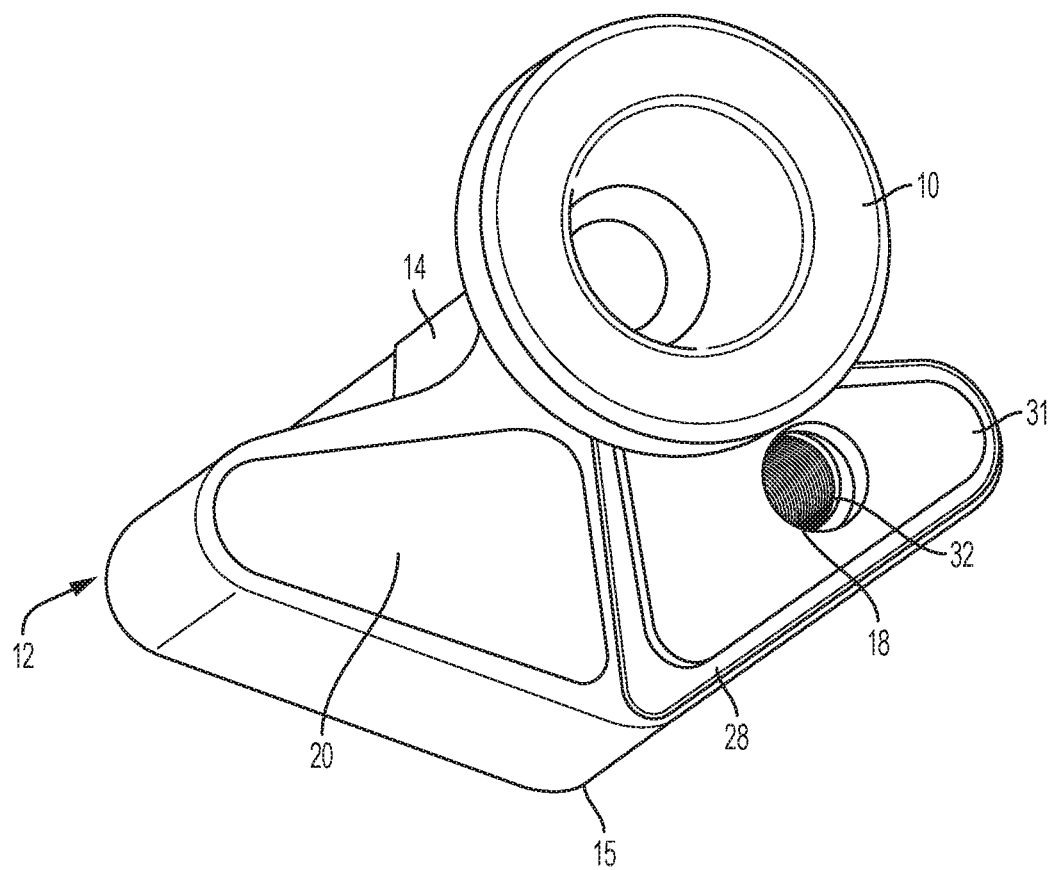
FIG. 4 shows a perspective view of an embodiment of a cleaning device and trocar.

With reference to FIGS. 3 and 4, sponge 20 is shown in its installed position in first depression 24 in casing 15. Sponge 20 may be comprised of any material known in the art. Sponge 20 may be used for cleaning debris and/or fluid from a scope. Sponge 20 also may be impregnated with a cleaning medium 22, such as a cleaning and/or defogging fluid. In an embodiment, cleaning medium 22 and or sponge 20 may be sterile.

FIG. 4 shows the trocar 10 with an embodiment of cleaning device 12 from a different angle than the previous figures. Holes in microfiber cover 31 and heating chamber cover 28 create the scope access hole 32, which allows a scope to access heating chamber 33 in second depression 26, where heating coil 16 may warm and aid in defogging a scope. Debris may be wiped from a scope's optical components by surgical staff on microfiber cover 31 and/or sponge 20, which may be impregnated with cleaning medium 22.

Figure 5:
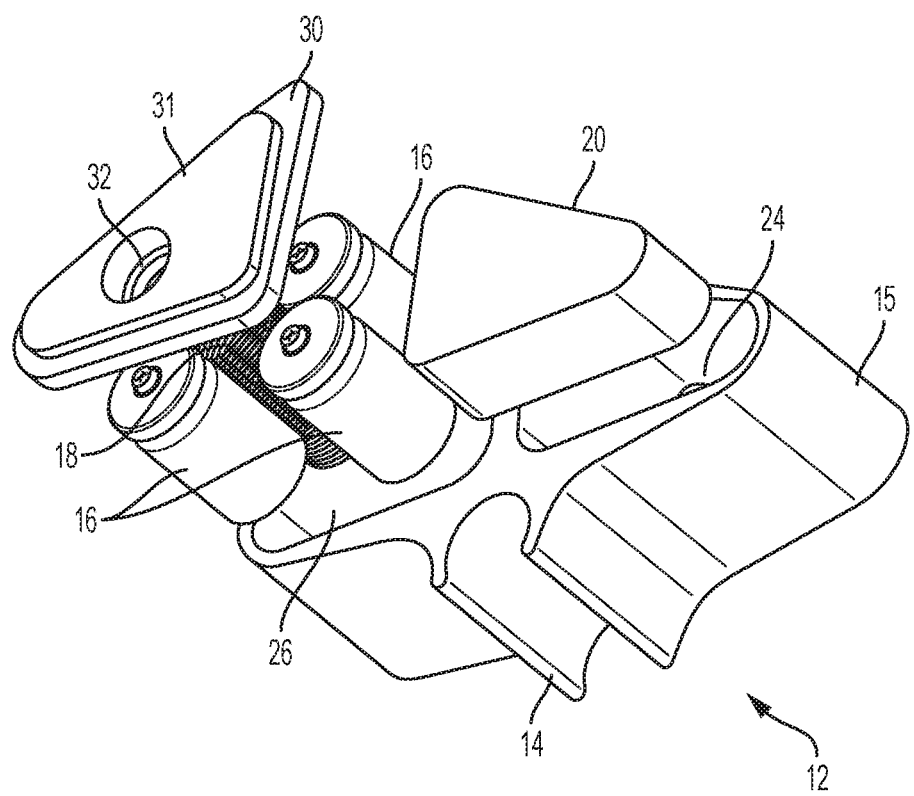
FIG. 5 shows an exploded view of an embodiment of a cleaning device.

FIG. 5 is another exploded view of the cleaning device 12 having the casing 15. The casing 15 comprises an attaching mechanism, such as snap member 14, which is configured to attach to a trocar. Snap member 14 is configured to removably attach to trocar 10. Other embodiments of casing 15 may be configured to attach to trocar 10 with tape, a friction fit, or through another mechanism otherwise known in the art.

The casing 15 also comprises a first depression 24, which is configured to hold a sponge 20. The sponge 20 may be at least partially moistened with a cleaning solution. The casing 15 also comprises second depression 26 which is configured to hold batteries 16 and heating coil 18 or a defogger, and forms heating chamber 33. Second depression 26 may hold one or more batteries 16, which in an embodiment includes three lithium batteries. In other embodiments, other types of batteries 16 may be used or adapted for use, and other numbers of batteries may be used. In another embodiment, another heating source, other than an electrical or battery-powered heating source, could be utilized, such as a chemical heat source or chemical heat pack, which would avoid the use and ultimate disposal of batteries, which can present challenges due to the potential environmental impact of battery waste.

The second depression 26 and heating chamber 33 of the casing 15 may be at least partially covered by a heat chamber cover 28. The heat chamber cover 28 may comprise the microfiber holder 30 and a scope access hole 32. A scope or microscope may be inserted into the scope access hole 32 and through the heating coil 18 or defogger. The scope or microscope may be wiped on the microfiber cover 31 disposed in the holder 30 before or after insertion into the scope access hole 32.

In at least one possible embodiment, a structure or material, such as double-sided adhesive tape, could be connected or attached to the casing 15, such as the side or underside, to allow the casing 15 to be connected or attached to a support structure.

Figure 6:
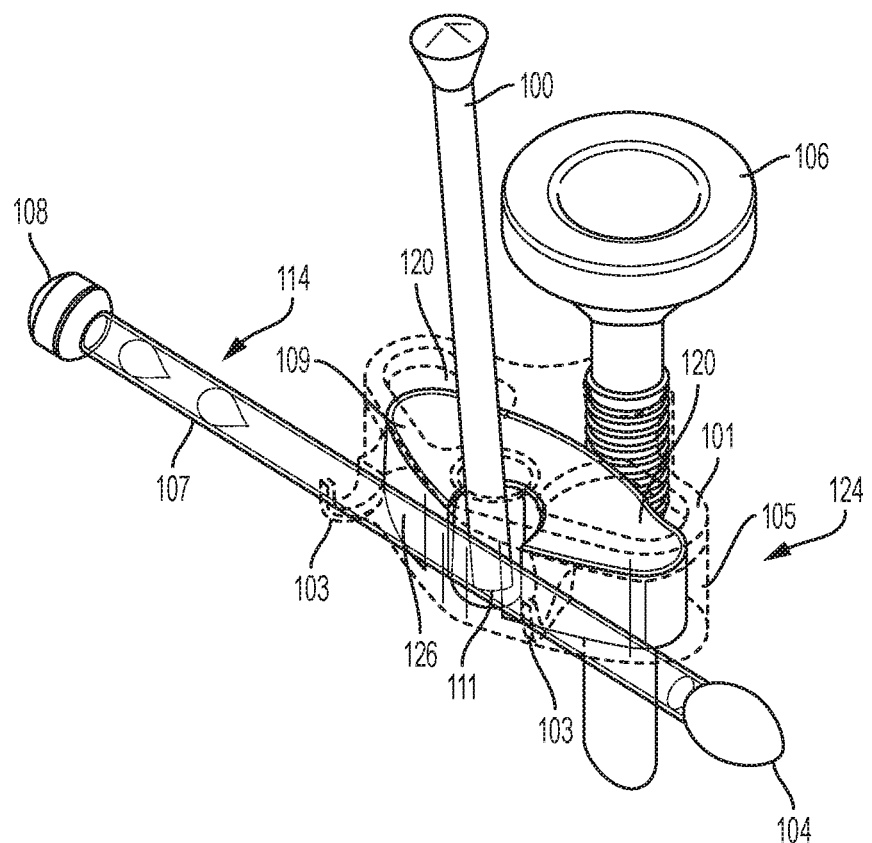
FIG. 6 shows a partially transparent perspective view of an embodiment of a cleaning kit attached to a trocar or cannula.

FIG. 6 shows a partially transparent view of an embodiment of a cleaning kit 124 attached to a trocar 106. The kit 124 includes a container 105 that may house a sponge 110, which may be impregnated with a cleaning solution, and a heater 109. A cover 101 is located on top of the container 105. The cover 101 has an opening therein into which can be inserted a surgical viewing device 100, such as a scope, laparoscope, or microscope, such that the scope lens 111 is inside the container 105. In an embodiment, cover 101 may include one or more recesses 120, at least one of which contains a microfiber wipe or cleaner 102. Also shown is a cannula cleaner 114, which is held by two cannula cleaner tube holders 103. Holders 103 may removably secure the cannula cleaner 114 to the container 105 when it is not in use during a surgical procedure. Cannula cleaner 114 may be secured by a friction fit, or in some other manner otherwise known in the art. In addition, the cover 101 may have one or more projections 126 that project out above the cannula cleaner 114 to further secure the cannula cleaner 114 in place in a secured position on container 105.

An embodiment of cannula cleaner 114 may include an elongated body with a cleaning tip 104 disposed at one end. In an embodiment the body of the cannula cleaner 114 may comprise a tube that also functions as a solution container 107. On the end opposite the cleaning tip 104 is located a solution dispensing valve 108. Either the valve 108 or the solution container 107 may be squeezed or pinched or pressed in to cause an amount of a cleaning or defogging solution, or some other liquid known in the art, to be dispensed. The solution may be dispensed into the container 105. By containing the solution in the cannula cleaner 114, a supply of cleaning solution is readily available to be dispensed into the container 105, and is in easy reach for a user of the trocar 106 and cleaning kit 124, such as by a surgeon or other medical professional. By mounting the cannula cleaner 114 on the container 105, the cannula cleaner 114 is easy to reach for use in cleaning or clearing out the trocar 106. The design of the cannula cleaner 114 therefore combines a cleaning device with a cleaning solution supply, so as to facilitate keeping the trocar 106 and viewing instruments clean during a surgical procedure. However, it should be understood that other embodiments of cannula cleaner 114 may exist, such as an embodiment that does not hold solution and lacks a solution dispensing valve 108. Another embodiment may include cleaning tips 104 at both ends of the cleaning device 114. In such an embodiment, the cleaning tips 104 may be of the same size, or of different sizes. Cannula cleaning tip 104 may be comprised of a sponge, foam, microfiber, or some material otherwise known in the art.

Figure 7:
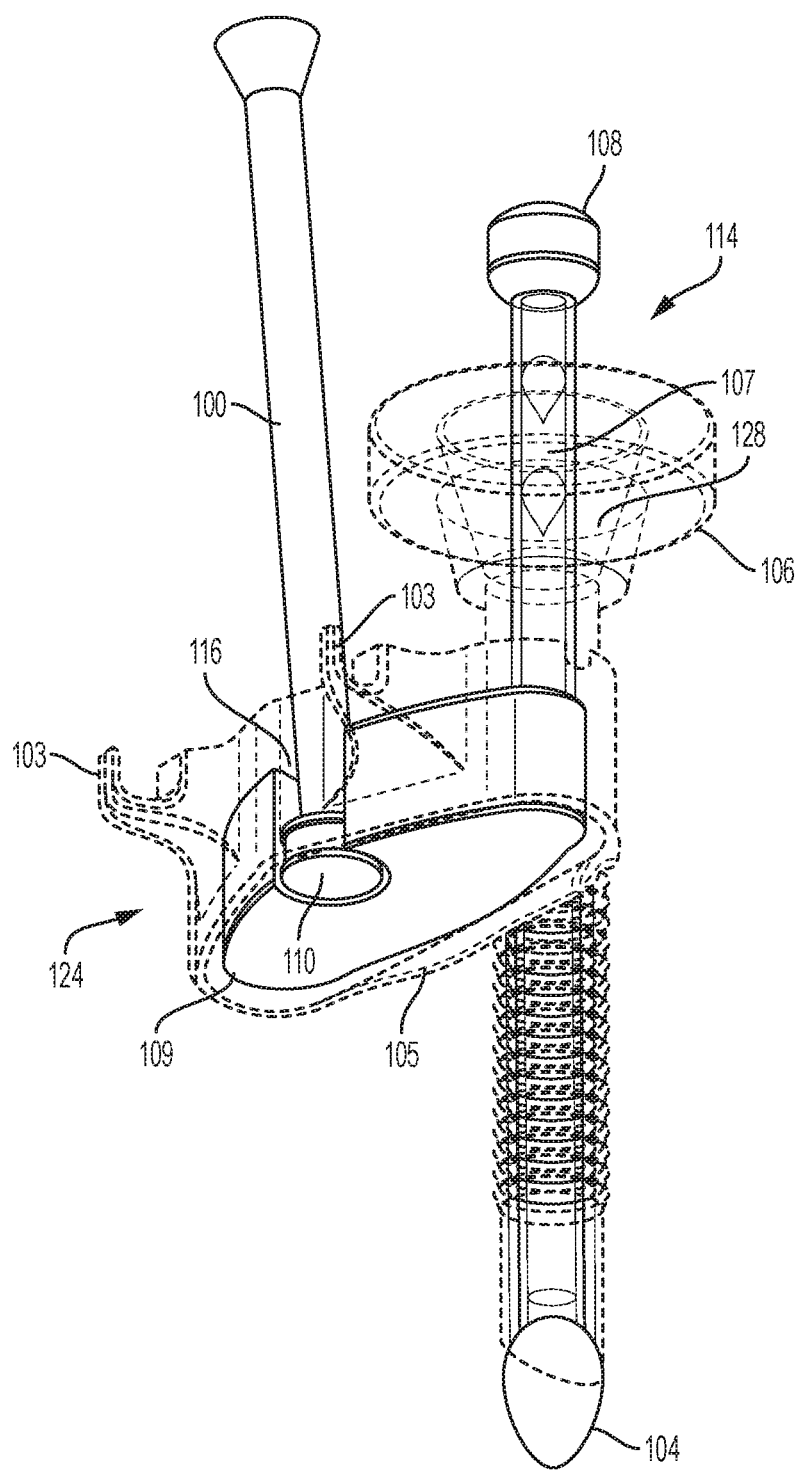
FIG. 7 shows another view of an embodiment of a cleaning kit shown in FIG. 6.

FIG. 7 shows another view of the cleaning kit 124 shown in FIG. 6. In FIG. 7, container 105 is shown as transparent in order to demonstrate how scope 100 may be inserted through scope access hole 116, so that the optics thereof may contact sponge 110. However, it should be understood that not all embodiments of base 105 need be transparent. FIG. 7 also depicts how scope 100 may interact with an embodiment of heater 109. In an embodiment, heater 109 may be configured to surround or partially surround scope 100, and may substantially border the perimeter or part of the perimeter of sponge 110. Heater 109 and sponge 110 may be configured to create a substantially cylindrical space, where the lens 111 of a scope 110 may be inserted for cleaning and/or defogging, which may be preferable to engage embodiments of scopes 100 that are substantially cylindrically-shaped. In an embodiment, sponge 110 may be configured to maximize efficient contact with lens 111 of scope 100. In an embodiment, sponge 110 may be substantially circular in shape. Embodiments of heater 109 may comprise other shapes. Embodiments of heater 109 may use electrical or chemical processes to generate heat, or may do so using another manner known in the art.

With further reference to FIG. 7, cannula cleaner 114 may be inserted into the cannula 128 of trocar 106 to clean the cannula 128 of fluids, condensates, and/or debris. In an embodiment, cannula cleaning tip 104 may be inserted into cannula 128. In an embodiment, cannula cleaning tip 104 may have a diameter that is substantially the same or larger than the diameter of the cannula 128. Cannula cleaning tip 104 may be comprised of a deformable material, and deform to fit into cannula 128 while contacting the walls of the cannula 128. Cannula cleaning tip 104 may be sufficiently absorptive to absorb fluids and/or condensate present in trocar 106. Trocar 106 is shown as transparent in order to better illustrate the insertion of cannula cleaner 114 therein; however, it should be understood that embodiments of trocar 106 need not be transparent.

Figure 8:
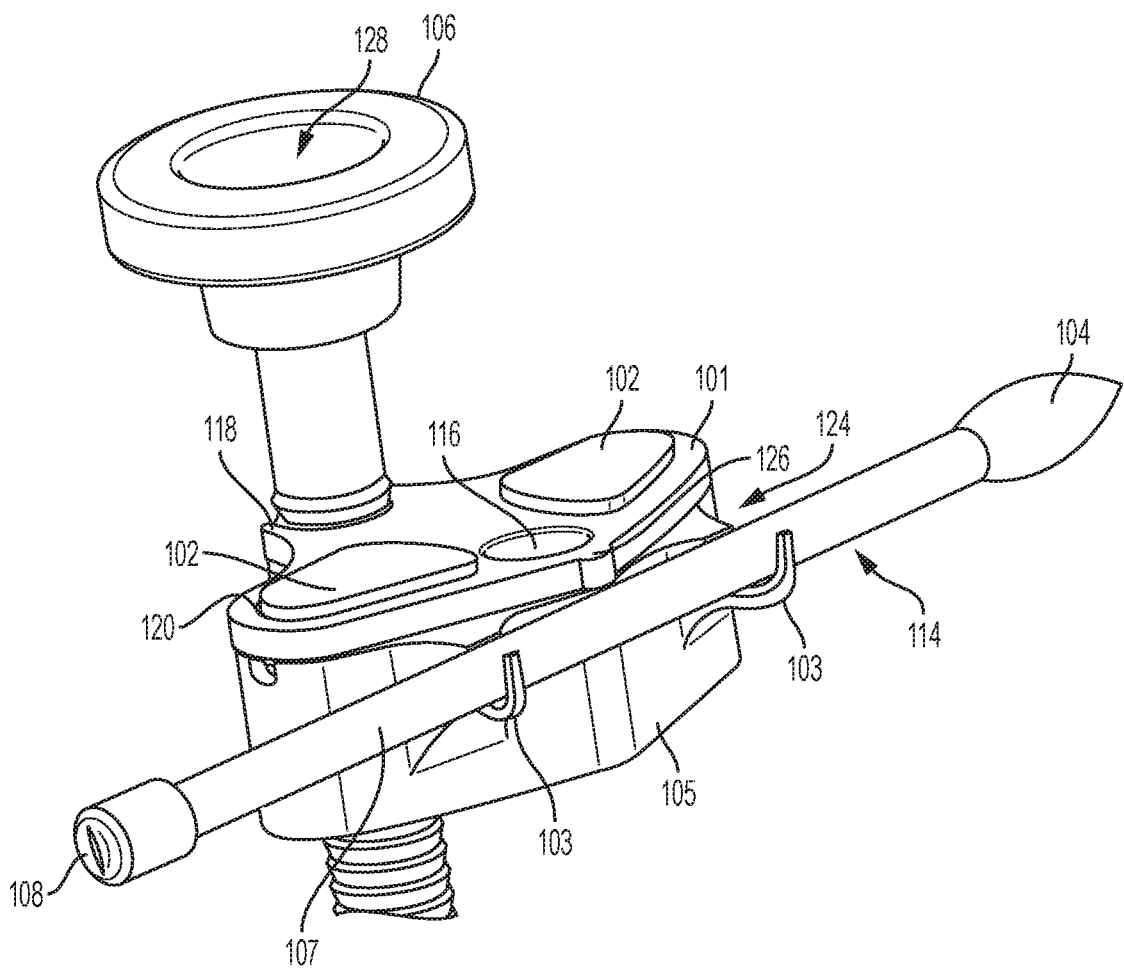
FIG. 8 shows another view of an embodiment of a cleaning kit shown in FIG. 6.

FIG. 8 shows perspective view of the cleaning kit 124 depicted in FIG. 6. Cannula cleaner 114 is shown disposed on cannula holders 103, which are configured to contain cannula cleaning device 114 against container 105 during a surgical procedure when cannula cleaner 114 is not in use. In an embodiment, cover 101 of cleaning kit 124 may include projection 126 that is configured to further constrain cannula cleaner 114 when not in use. Cover 101 may include one or more microfiber wipes 102 disposed thereon to further aid in cleaning debris or condensate from a scope 100. While the embodiment shown in FIG. 8 shows a configuration wherein two microfiber wipes 102 are positioned on cover 101 roughly on either side of scope access hole 116, it should be understood that other configurations or numbers of wipes 102 may be used. It also should be understood that embodiments of cover 101 need not include microfiber wipes 102, and that other materials or wiping elements otherwise known in the art may be used to wipe debris from the lens 111 of a scope. Wipes 102 may be disposed in one or more recesses 120 in cover 101. Cleaning kit 124 may removably attach to trocar 106 by a snap member 118, or another manner known in the art.

Figure 9:
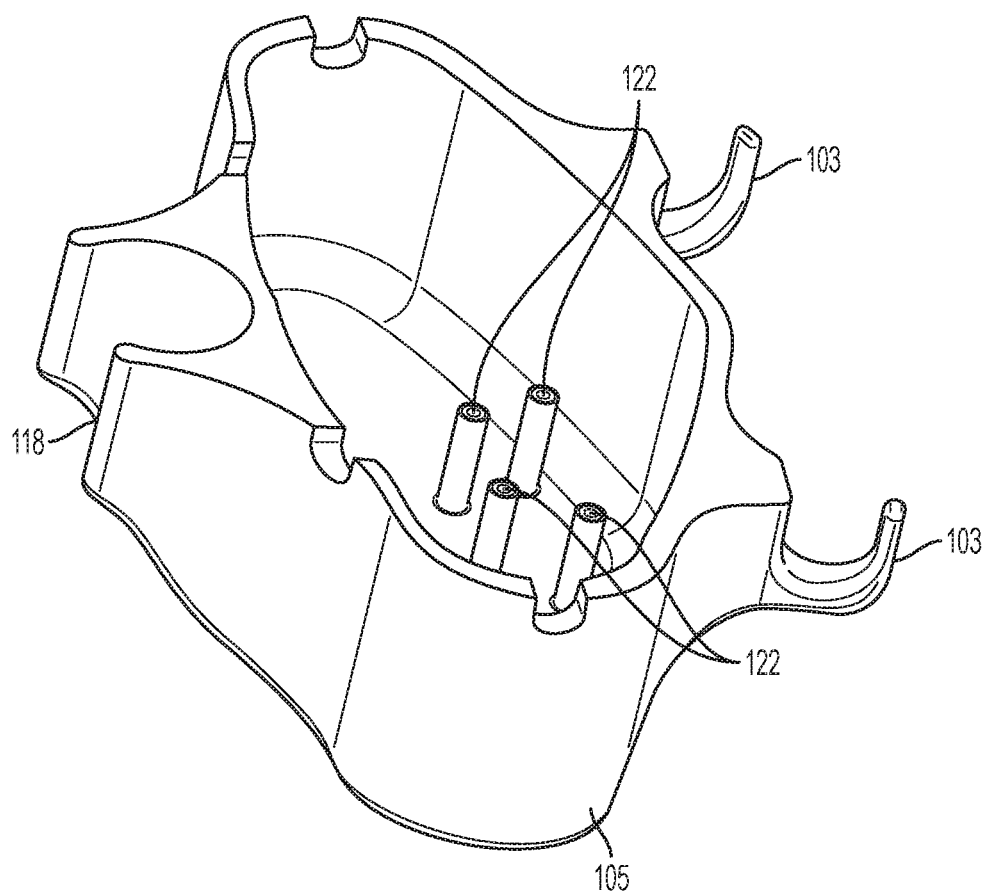
FIG. 9 shows a view of a container of an embodiment of the cleaning kit shown in FIG. 6.

FIG. 9 shows a perspective view of a portion of the container 105 of the cleaning kit 124 shown in FIG. 6. An embodiment of container 105 may be integrally molded with snap member 118 and/or one or more cannula cleaning device holder 103. The interior of container 105 may comprise a single chamber, or multiple chambers. The at least one chamber may include one or more support posts 122. Support posts 122 may provide support for cover 101, and may provide support for configurations of heater 109. In embodiments of heater 109, posts 122 may support configurations of batteries, a heating coil, chemical packs, or other components of a heater 109 otherwise known in the art.

Figure 10:
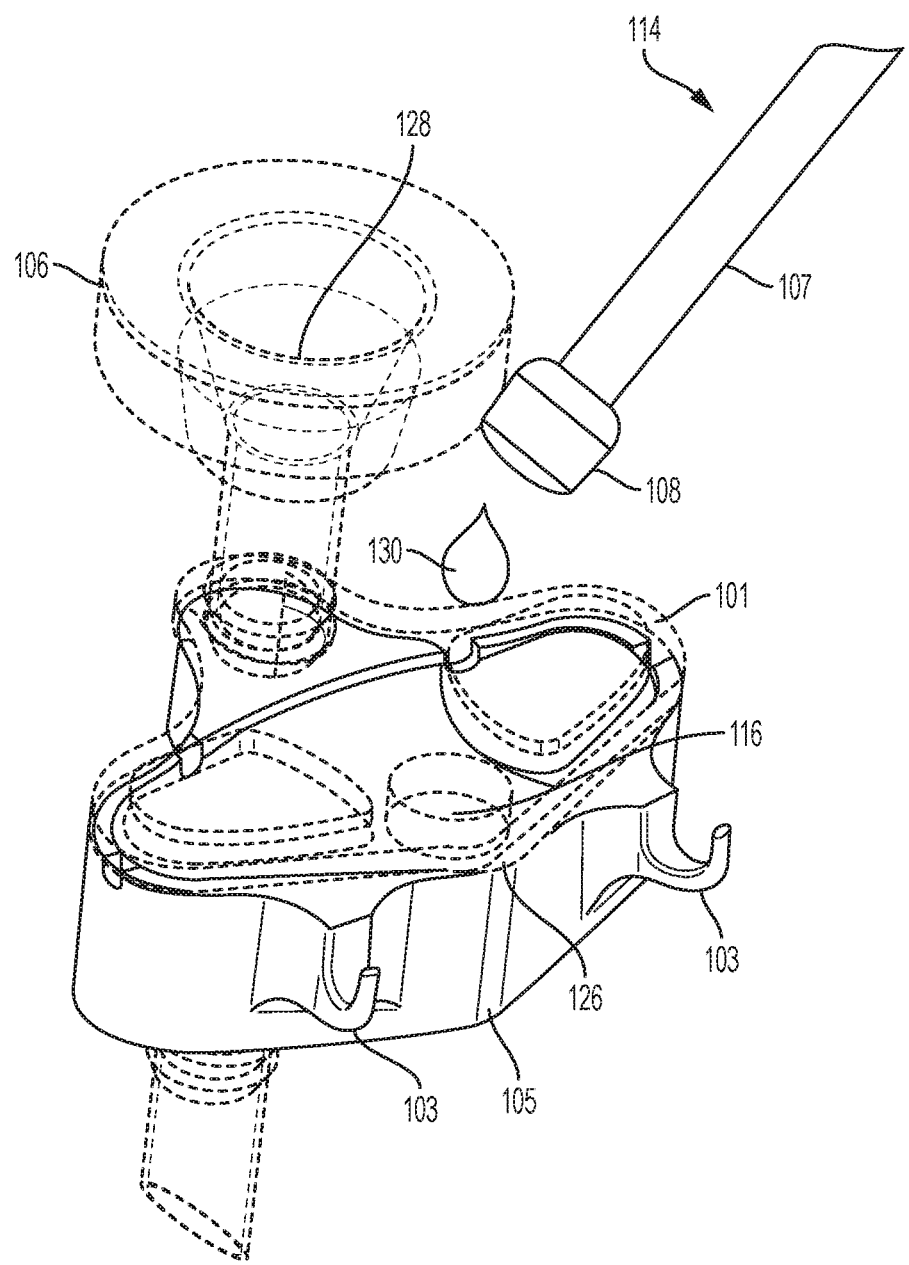
FIG. 10 shows another view of the embodiment of a cleaning kit shown in FIG. 6, with a cannula cleaner being used to dispense cleaning medium.

FIG. 10 shows another view of the cleaning kit 124. In an embodiment, cannula cleaner 114 may be used to dispense cleaning and/or defogging solution into container 104 through scope access hole 116. In an embodiment, solution may exit solution container 107 of cannula cleaner 114 through solution dispensing valve 108. When solution— represented by a droplet of cleaning solution 130—enters through scope access hole 116, it may contact and be absorbed by sponge 110. A scope may then be inserted into container 105 through scope access hole 116 and contact impregnated sponge 110, which may aid in cleaning and/or defogging the scope 110.

Figure 11:
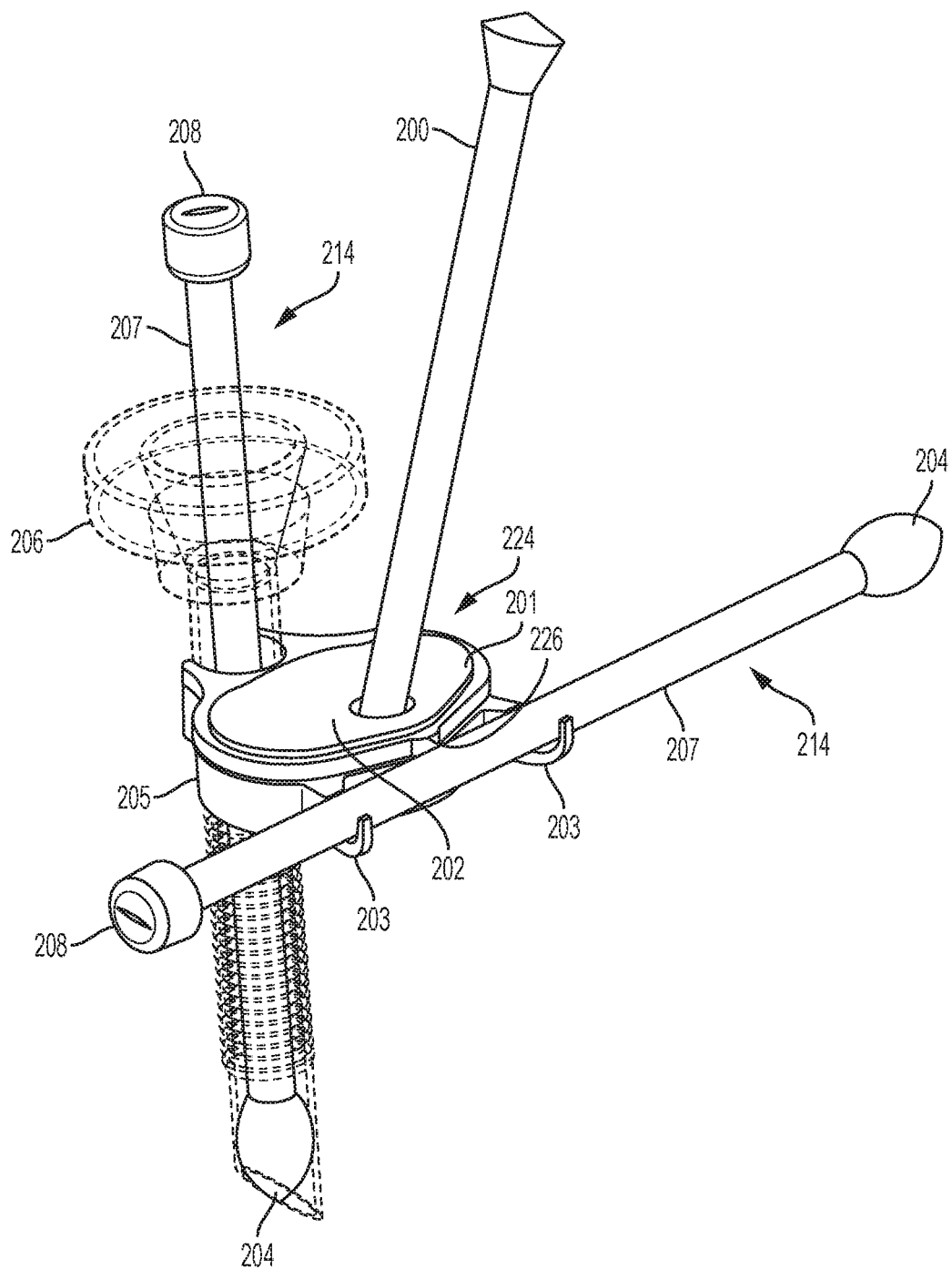
FIG. 11 shows an embodiment of a cleaning kit.
Figure 12:
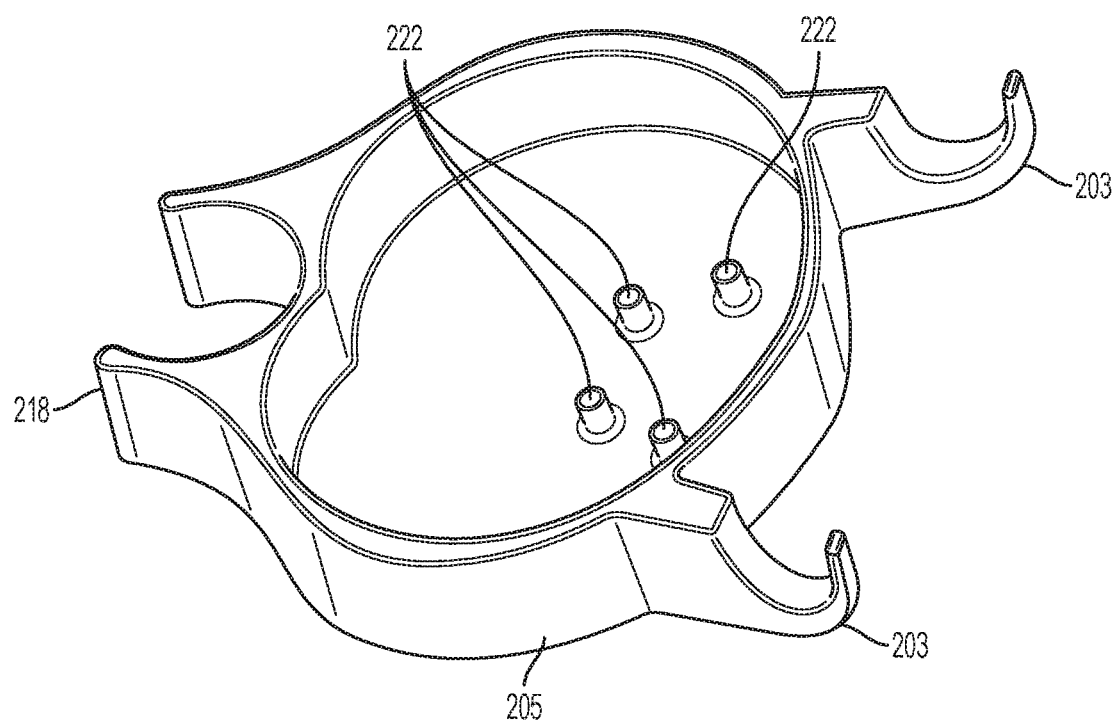
FIG. 12 shows a view of a container of an embodiment of a cleaning kit shown in FIG. 11.

With reference to FIGS. 11 and 12, an alternative embodiment of a cleaning kit 224 is illustrated. Cleaning kit 224 is configured to clean lens 211 of a scope 200 and may include a container 205 that is shorter or thinner than the embodiment of the container 105 shown in FIG. 6. In the example in FIG. 11, no batteries are utilized, so a shorter or thinner container 205 can be utilized. In an embodiment, may use no heating device or heating medium. In another embodiment, a chemical heating medium or chemical heating pack may be used which takes up less space than batteries. The cover 201 also may include a microfiber wipe or pad 202 that spans most or all of the surface area of cover 201. FIG. 11 depicts two cannula cleaners 214 in order to demonstrate both insertion into trocar 206, and placement in cleaner tube holders 203. However, it should be understood that not all embodiments of cleaning kit 224 require more than one cannula cleaner 214. Each of the cannula cleaners may include a cannula cleaning tip 204 at a first end thereof, a solution container 207 extending between the first end and second end thereof, and a solution dispensing valve 208 positioned at the second.

FIG. 12 shows a view of container 205 of the embodiment of the cleaning kit 224 shown in FIG. 11. In an embodiment, snap member 218 and one or more cannula cleaner holders 203 may be integrally molded with container 205. The container 205 may comprise a chamber, and may include one or more internal supports 222. In one example, internal supports 222 may be used to support cover 201, or constrain heater 209 and/or sponge 210.

It is to be understood that the invention may assume various alternative variations, except where expressly specified to the contrary. It is also to be understood that the specific devices illustrated in the attached drawings, and described in the specification, are simply exemplary embodiments of the invention. Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope thereof. For example, it is to be understood that the present invention contemplates that, to the extent possible, one or more features of any embodiment can be combined with one or more features of any other embodiment. The embodiments

The invention claimed is:

1. A cleaning device configured for cleaning a surgical scope during minimally invasive surgery comprising:
   a casing defining an interior and having an isosceles triangular shape, when viewed from a top or bottom view, the shape comprising two sides of equal length and a longer side, the casing comprising:
      a body comprising a closed bottom, an open top, and a sidewall extending between the bottom and the top; and
      a cover positioned over at least a portion of the open top, the cover comprising at least one opening for accessing the interior of the casing;
   a heating element disposed in the interior of the casing; and
   a snap member integrally molded with and extending from the longer side of the casing, the snap member comprising a first arm and a second arm extending radially away from the sidewall of the body of the casing and defining a cavity having a partially circular cross section configured to receive and engage an outer surface of a tubular portion of a trocar to removably attach the casing to the trocar in a position in which a central longitudinal axis of the tubular portion of the trocar engaged by the snap member is spaced a fixed distance apart from the interior of the casing.

2. The cleaning device of claim 1, wherein the body and the cover collectively define the interior of the casing.

3. The cleaning device of claim 1, further comprising a sponge disposed in the interior of the casing.

4. The cleaning device of claim 3, wherein a lens portion of the surgical scope can be inserted through the at least one opening of the cover and brought into contact with the sponge.

5. The cleaning device of claim 3, wherein the sponge is impregnated with a cleaning and/or defogging fluid.

6. The cleaning device of claim 1, wherein the heating element comprises a heating coil.

7. The cleaning device of claim 6, wherein a central axis of the heating coil is parallel to the central axis of the tubular portion of the trocar engaged to the snap member.

8. The cleaning device of claim 6, further comprising a sponge positioned in the interior of the cavity, within a cylindrical volume defined by the heating coil.

9. The cleaning device of claim 8, wherein the sponge has a circular cross section, and wherein a peripheral edge of the sponge is bounded by the heating coil.

10. The cleaning device of claim 8, wherein a lens portion of the surgical scope can be inserted through the at least one opening of the casing and into the cylindrical volume defined by the heating coil.

11. The cleaning device of claim 1, wherein the heating element comprises at least one battery positioned within the interior of the casing for providing power for the heating element.

12. The cleaning device of claim 1, wherein the snap member supports the casing, so that a line normal to a bottom surface and passing through the opening of the casing is parallel to the central longitudinal axis of the tubular portion of the trocar engaged by the snap member.

13. The cleaning device of claim 1, further comprising a wiping element positioned in a recess within an outer surface of the casing.

14. The cleaning device of claim 1, wherein each arm of the snap member comprises an inwardly directed protrusion extending into the cavity for engaging the trocar to maintain the trocar within the cavity.

15. The cleaning device of claim 1, wherein the snap member maintains the casing in an upright orientation relative to the trocar, such that a longitudinal axis of the casing is parallel to the central longitudinal axis of the tubular portion of the trocar engaged by the snap member.

16. A trocar assembly for introducing a surgical scope to a body during a minimally invasive surgery, the assembly comprising:
   a trocar comprising a tubular portion comprising an outer surface; and
   a cleaning device mounted to the trocar configured for cleaning the surgical scope, the cleaning device comprising:
      a casing defining an interior, the casing comprising:
         a body comprising a closed bottom, an open top, and a sidewall extending between the bottom and the top; and
         a cover positioned over at least a portion of the open top, the cover comprising at least one opening for accessing the body;
      a heating element disposed in the interior of the casing; and
      a snap member integrally molded with the body of casing comprising a first arm and a second arm extending radially away from the sidewall of the body of the casing and defining a cavity having a partially circular cross section configured to receive and engage the outer surface of the tubular portion of the trocar to removably attach the casing to the trocar in a position in which a central longitudinal axis of the trocar is spaced a fixed distance apart from the interior of the casing.

17. The trocar assembly of claim 16, wherein the snap member supports the casing, so that a line normal to a bottom surface and passing through the at least one opening of the cover is parallel to the central longitudinal axis of the tubular portion of the trocar engaged by the snap member.

18. The trocar assembly of claim 16, wherein the heating element comprises a heating coil, and wherein a central axis of the heating coil is parallel to the central axis of the tubular portion of the trocar engaged to the snap member.

* * * * *